United States Patent
Sonderegger et al.

(10) Patent No.: US 10,105,484 B2
(45) Date of Patent: Oct. 23, 2018

(54) INSULIN INFUSION SET

(75) Inventors: Ralph Lee Sonderegger, Farmington, UT (US); Victor Isaac Politis, Framingham, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 488 days.

(21) Appl. No.: 13/984,025

(22) PCT Filed: Feb. 8, 2012

(86) PCT No.: PCT/US2012/000071
§ 371 (c)(1),
(2), (4) Date: Nov. 20, 2013

(87) PCT Pub. No.: WO2012/108957
PCT Pub. Date: Aug. 16, 2012

(65) Prior Publication Data
US 2014/0074033 A1     Mar. 13, 2014

Related U.S. Application Data

(60) Provisional application No. 61/441,261, filed on Feb. 9, 2011.

(51) Int. Cl.
*A61M 5/158* (2006.01)

(52) U.S. Cl.
CPC ..... *A61M 5/158* (2013.01); *A61M 2005/1587* (2013.01)

(58) Field of Classification Search
CPC .......... A61M 5/14244; A61M 5/14248; A61M 5/158; A61M 2005/14252; A61M 2005/1585; A61M 2005/1586; A61M 2005/1587; A61M 2005/1581; A61M 2005/1583; A61M 2005/1588; A61M 5/1582; A61M 5/3287; A61M 5/002; A61M 5/003; A61M 25/02; A61M 25/06; A61M 25/0606; A61M 25/0612; A61M 2025/0253; A61M 2025/028

USPC ......... 604/164.01, 167.01, 167.02, 533, 534, 604/535, 158

See application file for complete search history.

(56) References Cited

U.S. PATENT DOCUMENTS 4,747,831 A      5/1988  Kulli
4,813,937 A *    3/1989  Vaillancourt ......... A61M 5/145
                                             128/DIG. 12
(Continued)

FOREIGN PATENT DOCUMENTS

JP      11-347120        12/1999
JP      2010-051702      3/2010
(Continued)

*Primary Examiner* — Kevin C Sirmons
*Assistant Examiner* — Leah Swanson
(74) *Attorney, Agent, or Firm* — Dickinson Wright PLLC

(57) ABSTRACT

An insulin infusion set (30) for use with an inserter (40) is disclosed. The infusion set (30) includes an extension set (50). The extension set (50) includes a housing (70), a base (90) and a latching device (82). The base (90) houses a base septum (120) and an infusion cannula (42). The latching device (82) releasably attaches the housing (70) to the base. When the housing (70) is attached to the base (90), a part of the housing (70) extends into and opens the base septum (120).

16 Claims, 8 Drawing Sheets

(56) References Cited

U.S. PATENT DOCUMENTS

| | | | |
|---|---|---|---|
| 5,176,662 A * | 1/1993 | Bartholomew | A61M 25/0606 |
| | | | 128/DIG. 26 |
| 5,501,675 A | 3/1996 | Erskine | |
| 5,575,777 A | 11/1996 | Cover et al. | |
| 5,700,250 A | 12/1997 | Erskine | |
| 5,702,367 A | 12/1997 | Cover | |
| 5,795,339 A | 8/1998 | Erskine | |
| 5,830,190 A | 11/1998 | Howell | |
| 5,957,891 A | 9/1999 | Kriesel et al. | |
| 6,017,328 A | 1/2000 | Fischell et al. | |
| 6,582,402 B1 | 6/2003 | Erskine | |
| 2002/0123724 A1 | 9/2002 | Douglas et al. | |
| 2003/0176852 A1 | 9/2003 | Lynch et al. | |
| 2005/0101932 A1 * | 5/2005 | Cote | A61M 5/158 |
| | | | 604/506 |
| 2005/0107743 A1 * | 5/2005 | Fangrow, Jr. | A61M 5/158 |
| | | | 604/164.01 |
| 2005/0113761 A1 | 5/2005 | Faust et al. | |
| 2005/0256460 A1 | 11/2005 | Rome et al. | |
| 2007/0112303 A1 | 5/2007 | Liniger | |
| 2007/0225660 A1 | 9/2007 | Lynn | |
| 2008/0243083 A1 | 10/2008 | DeStefano et al. | |
| 2009/0143763 A1 | 6/2009 | Wyss et al. | |
| 2010/0057021 A1 * | 3/2010 | Ishikura | A61M 5/158 |
| | | | 604/288.01 |
| 2011/0054399 A1 | 3/2011 | Chong et al. | |

FOREIGN PATENT DOCUMENTS

| | | | |
|---|---|---|---|
| JP | 2011-520507 | 7/2011 | |
| WO | WO-2006/062680 A1 | 6/2006 | |
| WO | WO 2009139857 A1 * | 11/2009 | A61M 5/158 |
| WO | WO-2009139857 A1 | 11/2009 | |

* cited by examiner

INSULIN INFUSION SET

CROSS-REFERENCE TO RELATED APPLICATION

This application claims the benefit under 35 U.S.C. § 119(e) of U.S. Provisional Application No. 61/441,261, filed on Feb. 9, 2011 in the U.S. Patent and Trademark Office, the disclosure of said application being incorporated herein by reference in its entirety.

FIELD OF THE INVENTION

The present invention relates generally to infusion sets that can be inserted and attached to the skin using commercially available inserter devices.

BACKGROUND OF THE INVENTION

For patients with diabetes, there are two principal modes of daily insulin therapy. The first mode includes syringes and insulin pens. These devices are simple to use and are relatively low in cost, but they require a needle stick at each injection, typically three to four times per day. The second mode includes insulin infusion therapy, which utilizes an insulin pump. Infusion pumps, although more complex and expensive than syringes and pens, offer the advantages of continuous infusion of insulin via an infusion cannula, precision dosing, and programmable delivery schedules.

The use of an infusion pump requires the use of a disposable component, typically referred to as an infusion set, line set, extension set or pump set, which conveys the insulin from a reservoir within the pump into the skin of the user. An infusion set typically consists of a pump connector, a length of tubing, and a hub or base from which an infusion cannula (i.e., an infusion needle or a flexible catheter) extends. The hub or base has an adhesive which retains the base on the skin surface during use, and which may be applied to the skin manually or with the aid of a manual or automatic insertion device. In most cases, a detachable fluid connector is provided to allow the pump tubing to be disconnected from the hub or base of the infusion set when the user wishes to shower, bathe or swim.

Some infusion sets are complex in design and do not allow for adequate user mobility or for quick and simple methods to connect and disconnect the fluid connector from the base after the base has been attached to a user, while preventing external exposure of the inserted infusion cannula.

Accordingly, a need exists for improving infusion sets that will permit greater mobility for the user while preventing external exposure of the inserted infusion cannula.

SUMMARY OF THE INVENTION

An object of the present invention is to provide an infusion set that provides increased mobility for the user.

Another object of the present invention is to provide an infusion set that includes components that are able to self-close to prevent exposure of the infusion cannula.

Another object of the present invention is to provide a fluid path that is formed in an infusion set during use, with the fluid path being closed when the infusion set is not used.

These and other objects are substantially achieved by providing an infusion set that provides simplicity in manufacture and use for the convenience of the user, while preventing exposure of the lumen of the inserted infusion cannula to the external environment.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE EXEMPLARY EMBODIMENTS

Figure 1:
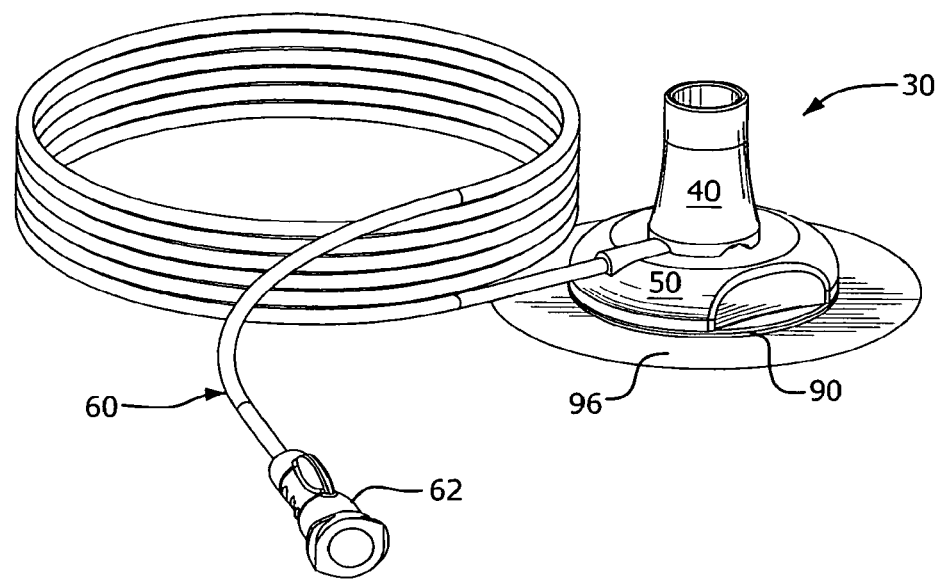
FIG. 1 is an enlarged perspective view of an exemplary infusion set connected to a tubeset.

An exemplary embodiment of a flexible catheter-type infusion set 30 in accordance with the present invention is illustrated in FIG. 1. The infusion set is intended to be connected to an infusion pump, for the delivery of insulin or other medicament. The infusion set may be used with existing commercial inserters, such as the Medtronic Quickserter® device, with little or no modification.

FIG. 1 illustrates a needle hub 40 that is positioned above an extension set 50, and a base 90 that is positioned below the extension set 50. Also illustrated is an adhesive pad 96 that is attached to an outer surface of the base 90. The adhesive pad 96 is configured to be attachable to a user. Also illustrated is a tube set or extension tube 60 that connects to the extension set 50. The connector 62 of the extension tube 60 connects to an infusion pump (not shown) such that medication such as insulin from the pump is delivered to the extension set 50.

Figure 2:
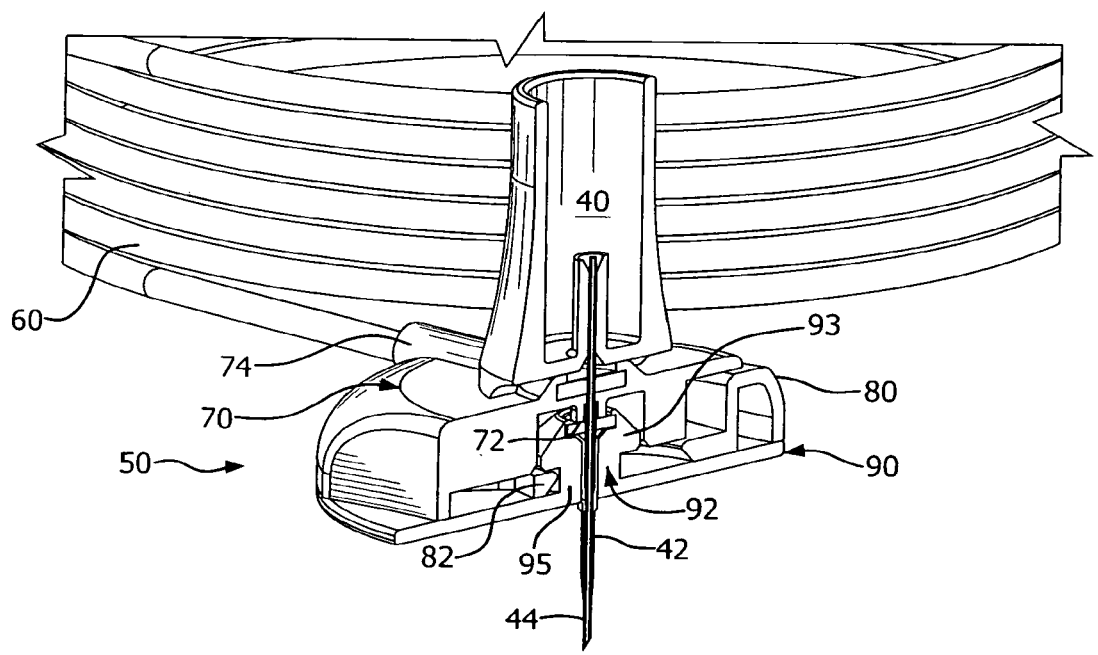
FIG. 2 is an enlarged cross-sectional view of the exemplary infusion set latched to a base.

The extension set 50 includes a housing 70. A button 80 is housed in the housing 70, as illustrated in FIG. 2. The button 80, when pressed, actuates a keyhole slot latching device 82.

FIG. 2 illustrates an exemplary embodiment of the present invention which shows a button latching configuration of the extension set 50, in which the housing 70, including the button 80, is latched onto the base 90. In this configuration, the button 80 is connected to a keyhole slot latching device 82 that engages the base retention boss 92 of the base 90, during the infusion state, to latch the housing 70 to the base 90.

More specifically, the boss 92 is mushroom-shaped and includes a cap portion 93 and a stem portion 95. When the keyhole slot latching device 82 is slotted between the cap 93 and the base 90 adjacent the stem portion 95, the housing 70 is latched onto the base 90, as illustrated in FIG. 2. The keyhole slot latching device 82 may frictionally engage one or more of the cap portion 93, stem portion 95 and a portion of the base 90 adjacent to the stem portion 95, in the latched state, as illustrated in FIG. 2.

The needle hub 40 is removed from the housing 70 after attaching a flexible catheter 42 to the user. Thereafter, when a user wishes to remove the extension set 50 from the base 90 that holds the catheter 42, the user presses the button 80 (shown in FIGS. 2-5) to unlatch the housing 70 from the retention boss 92, by actuating the keyhole slot latching device 82 to move from a latched position (see FIGS. 2 and 4) to an unlatched position (see FIGS. 3 and 5). In the unlatched state, the keyhole slot latching device 82 disengages from the slot position below the cap portion 93 and adjacent to the stem portion 95 of the retention boss 92, as illustrated in FIGS. 3 and 5.

In order to unlatch the housing 70 from the base 90 (after the needle hub 40 has been removed), the user presses the button 80, in the latched state (see FIG. 2), so that the button moves to a position shown in FIG. 3, wherein the keyhole slot latching mechanism 82 becomes disengaged from its slot position below the cap portion 93 and adjacent to the stem portion 95, whereupon the extension set 50 may be separated from the base 90.

Figure 3:
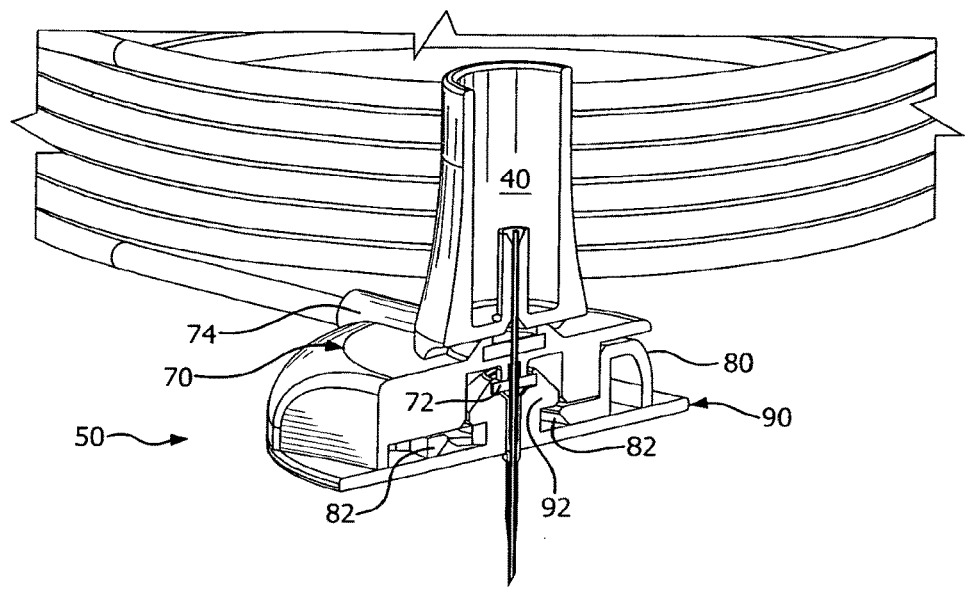
FIG. 3 is an enlarged cross-sectional view of the exemplary infusion set unlatched from a base.
Figure 4:
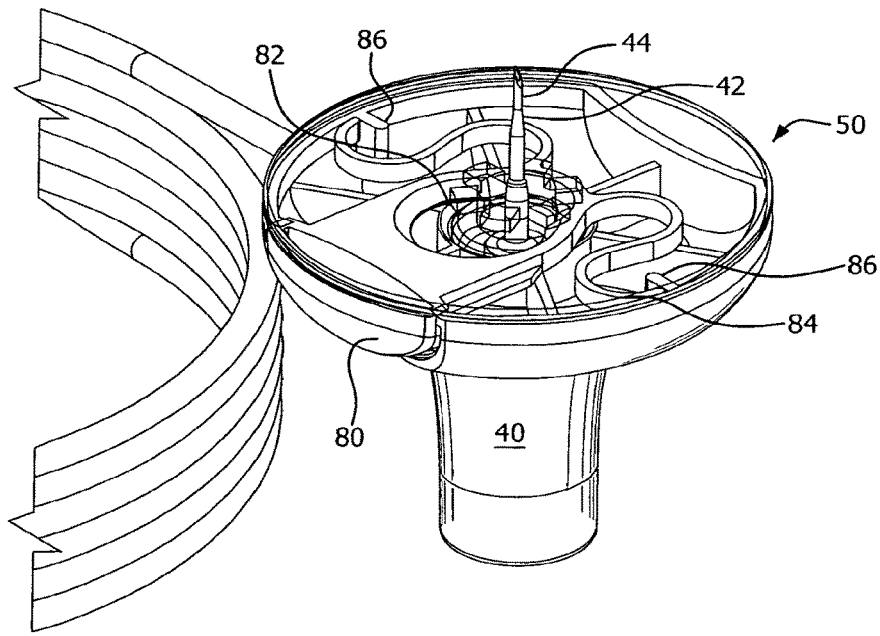
FIG. 4 is an enlarged perspective view of the exemplary infusion set illustrating a latched state.
Figure 5:
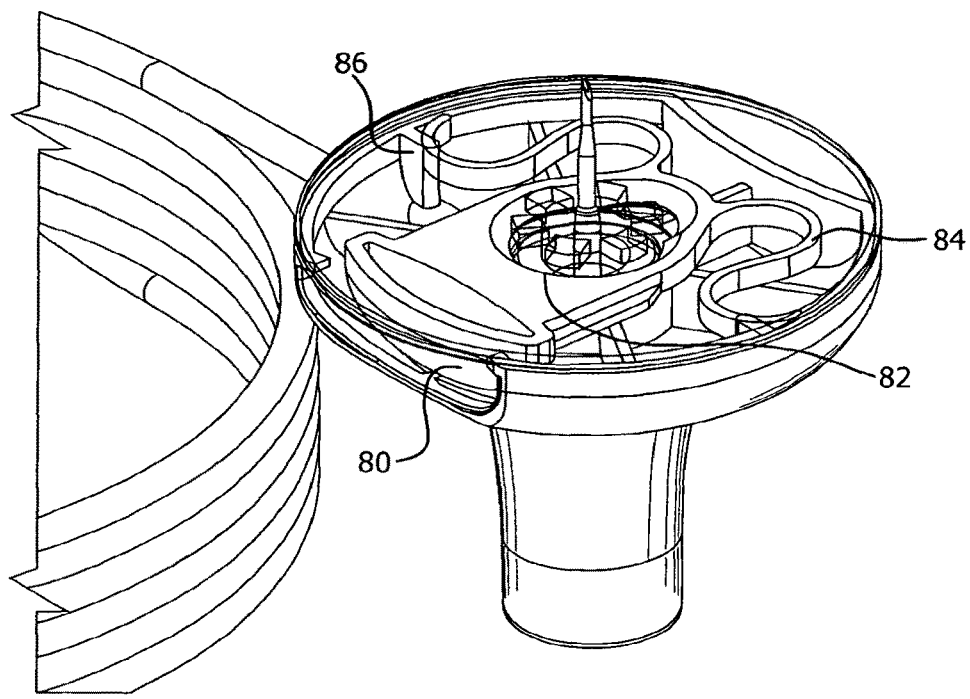
FIG. 5 is an enlarged perspective view of the exemplary infusion set illustrating an unlatched state.

The button 80 is shown with greater clarity in FIGS. 4 and 5, which depicts one configuration of a latching device, namely the keyhole slot latching device 82, with the base 90 illustrated as being transparent solely for visual clarity. The base 90 need not, in reality, be transparent as illustrated in the FIGS. 4 and 5. In the illustrated embodiment, an integrally molded set of plastic leaf springs 84 is actuated by the pressed button 80, to change from the latched state (FIGS. 2 and 4) to the unlatched state (FIGS. 3 and 5). The open ends of the leaf springs 84 are held in position by indents 86 that are positioned in the housing 70, as illustrated in FIG. 4. When the release button 80 is pressed, the leaf springs 84 disengage from the indents 86, as illustrated in FIG. 5.

FIGS. 3 and 5 show the button 80 in the unlatched position. In FIGS. 3 and 5, the keyhole slot latching device 82 has disengaged from the retention boss 92. The latching and unlatching mechanism illustrated in this embodiment uses a keyhole slot latching device 82 in which a keyhole having a smaller diameter portion and a larger diameter portion is included, wherein when the smaller diameter portion of the keyhole slot latching device 82 engages the retention boss 92, the housing 70 is latched onto the base 90, as illustrated in FIG. 2, wherein the outer wall of the smaller diameter portion of the keyhole slot latching device 82 engages the retention boss 92. When the button 80 is pushed, this actuates the disengagement of the housing 70 from the base 90, and as illustrated in FIGS. 3 and 5, the retention boss 92 is positioned at a central portion of the larger diameter of the keyhole slot latching device 82, thus disengaging the keyhole latching device 82 from the retention boss 92. This releases the housing 70 from the base 90.

Figure 6A:
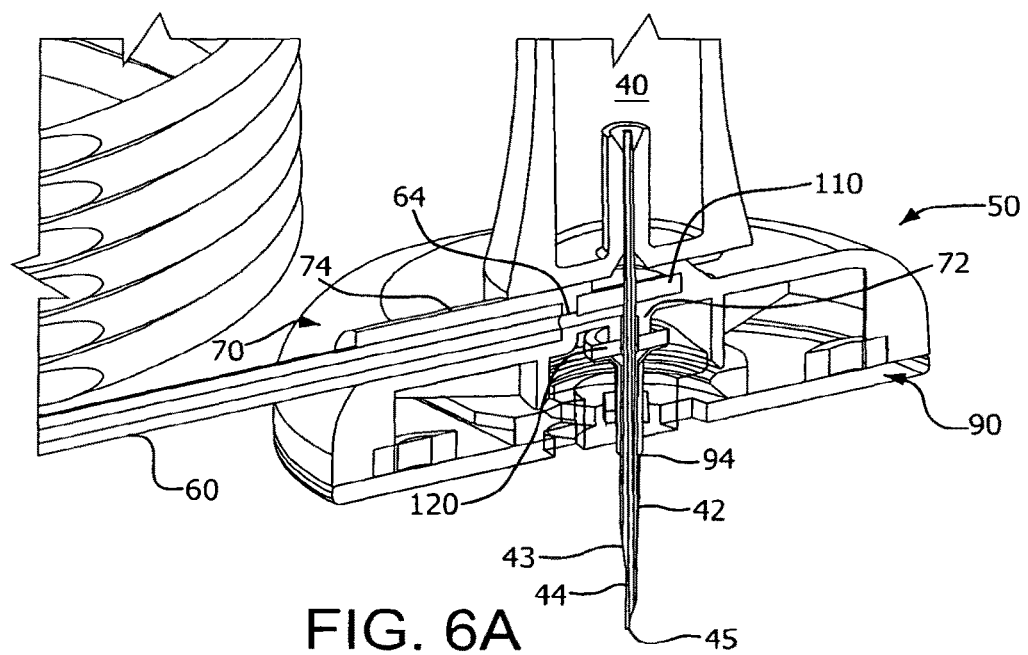
FIG. 6A is an enlarged cross-sectional view of the exemplary infusion set taken along a length of the tubeset receiver.

FIG. 6A illustrates a fluid path 64 that is formed along the tube set receiver 74 of the housing 70, as well as a pocket between the upper septum 110 and the lower septum 120, completed via an opening 94 in the base 90, a slot in the introducer needle 44, and the extension set tubing 60, enabling fluid to flow from a pump (not shown) attached to the connector 62 of the extension set tubing 60 through the tip 45 of the introducer needle 44, as illustrated in FIG. 6A. This allows the set 50 to be primed with the introducer needle 44 in place.

FIGS. 2, 3 and 6A illustrate the position in which the infusion set 30 can be attached to a user, either manually or with the aid of a commercially available or custom-designed inserter device. After the infusion set 30 has been attached to the user, the introducer needle 44 is removed by manually withdrawing the needle hub 40 from the housing 70. With reference to FIG. 6A, when the needle hub 40, to which the introducer needle 44 is attached, is removed, the introducer needle 44, which is secured to the needle hub 40, is pulled through both the upper septum 110 and the lower septum 120. When the introducer needle 44 moves out of the upper septum 110, the upper septum 110 self-closes its opening through which the introducer needle 44 has been removed, but the lower septum 120 remains open due to the presence of a blunt cannula 76 (illustrated in FIG. 6B) that extends from a central wall 72 of the housing 70, into the lower septum 120 in order to keep the lower septum 120 open.

Figure 6B:
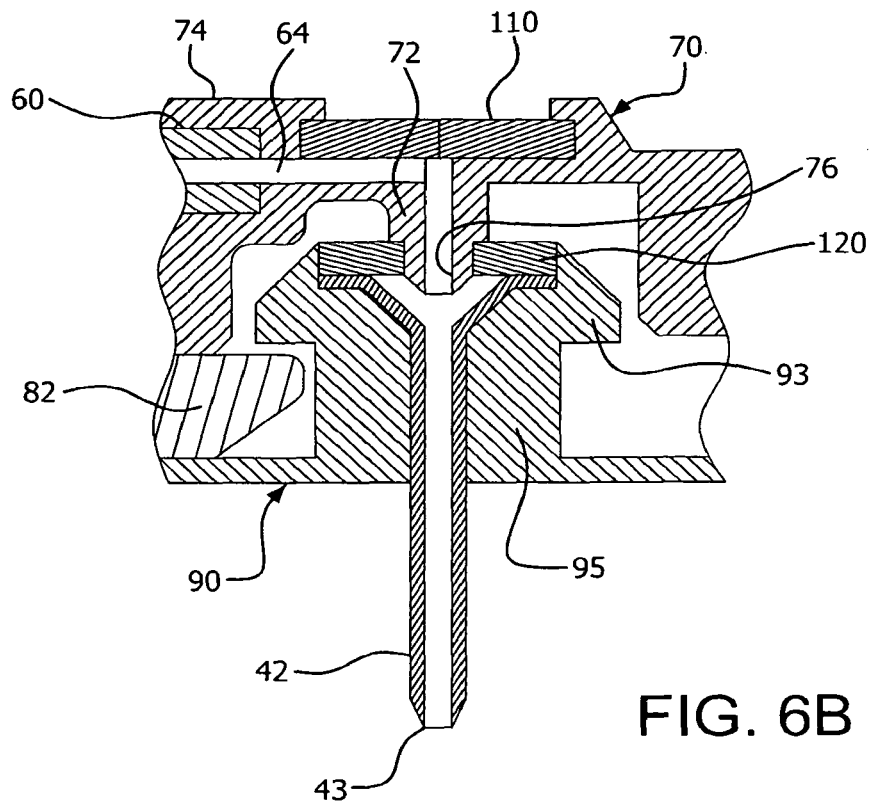
FIG. 6B is a cross-sectional view of a part of the infusion set without the introducer needle.
Figure 6C:
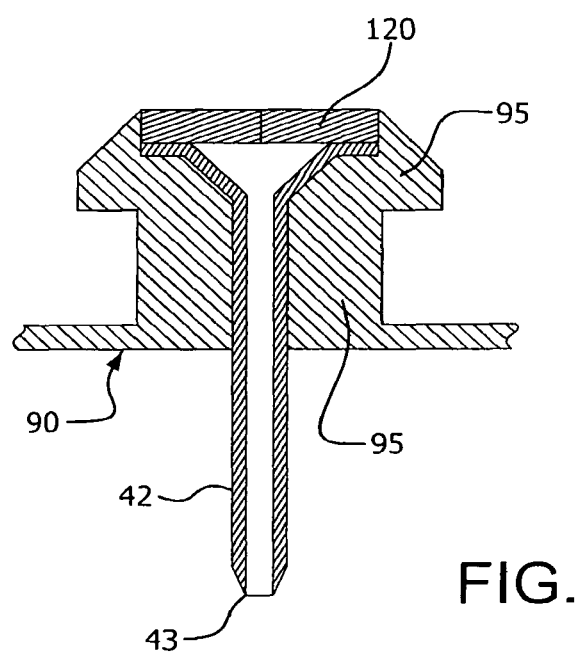
FIG. 6C is a cross-sectional view of a part of the infusion set of FIG. 6B after the housing has been removed from the base.

After the needle hub 40 and introducer needle 44 have been removed from the housing 70, the user receives medication from the pump through the fluid path 64, as shown in FIG. 6B, and out of the tip 43 of the catheter 42. If the user seeks to remove the housing 70 from the base 90, for instance prior to vigorous exercise, taking a shower or bath, or swimming, the user presses the button 80 to release the keyhole slot device 82 from the latched position (see FIGS. 2 and 4) to the unlatched position (see FIGS. 3 and 5), thereby unlatching the housing 70 from the base 90. The housing 70 can then be detached from the base 90 when the housing 70 is lifted from the base 90, in the same direction as the removal of the needle hub 40 from the housing 70. When the housing 70 is lifted from the base 90, the blunt cannula that extends from the central wall 72 of the housing 70 into the lower septum 120 is also removed, and thus the lower septum 120 is able to self-close its opening. Thus, when the housing 70 is removed from the base 90, the lower septum 120 becomes self-closed, preventing an external pathway from being formed into the inserted lumen of the catheter 42, thereby preventing introduction of external pathogens, liquids or gases into the catheter insertion site, as illustrated in FIG. 6C. The septum 120 is preferably provided with a pre-formed slit to facilitate penetration by the blunt cannula 76.

After the housing 70 has been removed from the base 90, the blunt cannula at the central wall 72 of the housing 70 can be capped or covered with a housing protective cap to prevent external exposure to the disconnected fluid path 64, after the housing 70 has been removed. Similarly, the base 90 can also be capped or covered with a suitably shaped cap, such as a base protective cap (not shown).

After the housing 70 has been removed, the catheter 42 remains attached to the base 90, with the lower septum 120 being self-closed (closing its hole) to prevent external contamination into the catheter 42, after the fluid path 64 has been disconnected by the removal of the housing 70, to which is attached the upper septum 110 (see FIG. 6C).

After the housing 70 has been detached from the base 90, the user has greater mobility to engage in vigorous exercise, swim, shower or bathe. After such activity has ended and the user wishes to reattach the housing 70 to the base 90, the user generally follows the following procedure.

If the base 90 was capped, the cap is removed, and the externally exposed outer surface of the lower septum 120 (facing toward the upper septum 110 in FIG. 6A) is sterilized by the user with any one of known methods for sterilization such as an alcohol wipe. If the blunt cannula of the central wall 72 was capped after the detachment of the housing 70 from the base 90, the cap (not shown) is then removed, and if the blunt cannula was not capped, the surface area thereof is also sterilized. Thereafter, the button 80 is pressed to position the housing 70 in the unlatched position, as in FIGS. 3 and 5. The housing 70 is then placed directly on the base 90 such that the blunt cannula of the central wall 72 of the housing 70 extends into and opens the closed hole of the lower septum 120, as illustrated in FIG. 6B. The button 80 is then released to latch the housing 70 onto the base 90 at the base retention boss 92, as illustrated in FIGS. 2, 4 and 6B. Thereafter, the fluid pathway 64 is reformed from the pump through the tubing 60, and into the housing 70, through the pocket between the upper septum 110 and the lower septum 120, and out through the tip 43 of the catheter 42, as illustrated in FIG. 6B.

Although FIGS. 2-6 illustrate a latching device that includes the button 80 connected to the keyhole slot latching device 82 that is secured onto the housing 70, any similar latching and unlatching device can be used to perform the same operation. For example, the embodiment that is illustrated in FIGS. 8-11 discloses another latching and unlatching device.

Figure 7A:
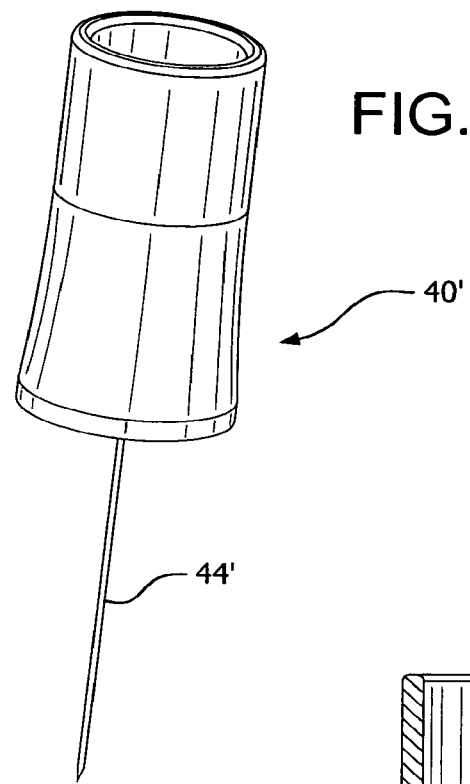
FIG. 7A is a perspective view of an introducer needle hub that is compatible with the exemplary infusion set.
Figure 7B:
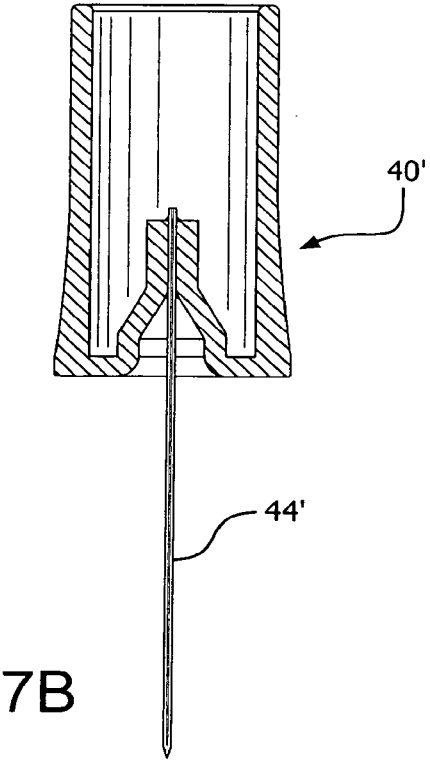
FIG. 7B is a cross-sectional view of the introducer needle hub of FIG. 7A.

FIGS. 7A and 7B illustrate a modified needle hub 40' to which is secured an introducer needle 44'. The needle hub 40' can have an outer diameter, height, inner diameter, and other dimensions such that it can be used with commercially available inserter devices, such as the Medtronic Quick-Set® inserter.

The infusion set 30' of FIGS. 8-11 functions substantially in the same manner as extension set 50 of FIGS. 1-6, but this embodiment uses a latching mechanism that is different from the keyhole slot latching device 82 and retention boss 92 of FIGS. 1-6. This embodiment also has an infusion set 30' that is designed to be used with a commercially available insertion device such as the Medtronic Quick-serter® insertion device.

Figure 8A:
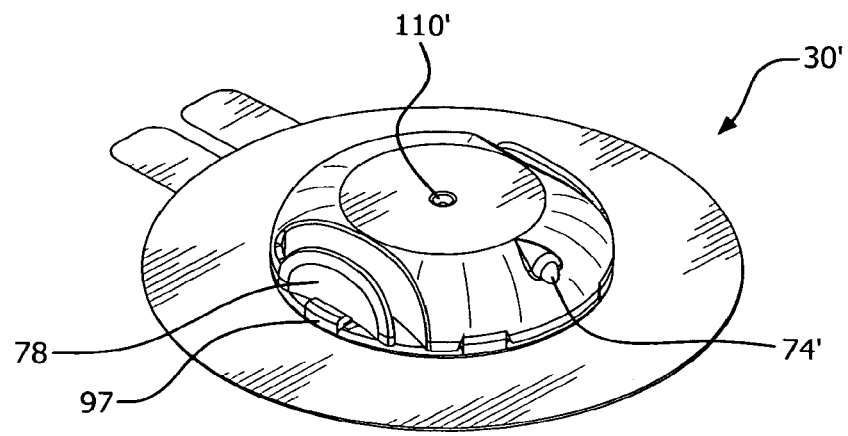
FIG. 8A is a perspective view of another exemplary infusion set.
Figure 8B:
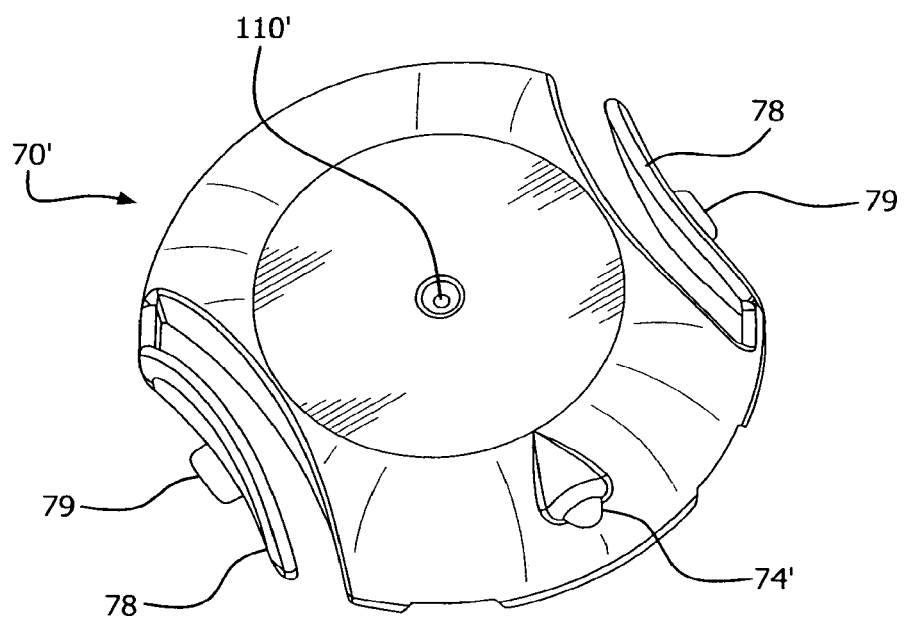
FIG. 8B is a perspective view of the housing or hub of the exemplary infusion set of FIG. 8A.
Figure 9:
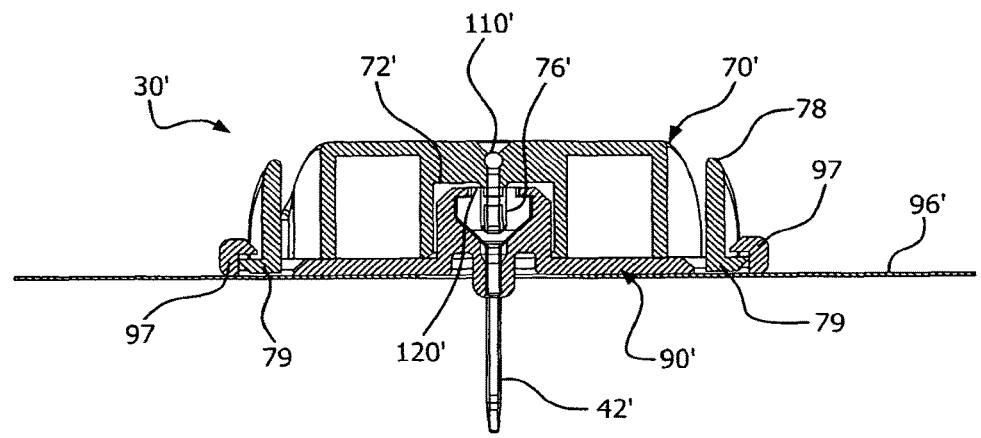
FIG. 9 is a cross-sectional view of the exemplary infusion set of FIG. 8A, illustrated with the housing attached to the base.
Figure 11:
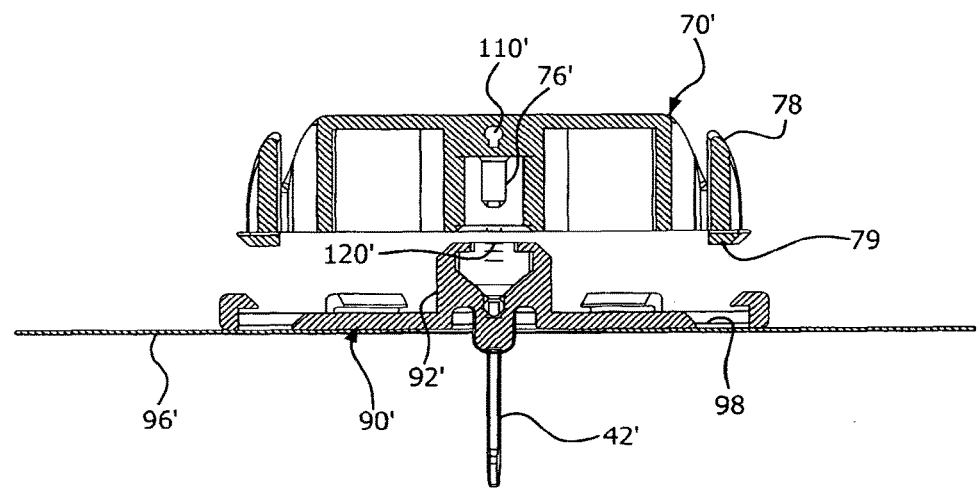
FIG. 11 is a cross-sectional view of the exemplary infusion set of FIG. 8A, illustrated with the housing detached from the base.

As illustrated in FIGS. 8 and 9, the infusion set 30' includes a housing or hub 70' that latches on to a base 90'. A release mechanism for disconnecting the hub 70' from the base 90' is integrated into the hub 70' and base 90', rather than being an extra component therein. The release mechanism includes a pair of levers 78, each having an arm 79. The levers 78 are hinged to the hub 70' and the levers 78 can be biased to manipulate the position of the arms 79. As illustrated in FIGS. 9-11, the base 90' includes radially positioned catches 97 that form pockets 98. The arms 79 of the levers 78 fit into the pockets 98 and interlock with the catches 97 in order to secure the hub 70' to the base 90', at one of six radial positions corresponding to each of the pockets 98.

In order to disconnect the hub 70' from the base 90', the user squeezes or biases the levers 78 of the hub 70', to position the arms 79 out of the pockets 98 of the base 90'. Thereafter, the user can lift the hub 70' from the base 90', to separate the two elements, as illustrated in FIG. 11.

In order to connect the hub 70' to the base 90' the user aligns the hub 70' adjacent the two opposing pockets 98 the user wishes to secure the arms 79 of the levers 78, biases the levers 78 offset from the pockets 98, rotates the hub 70', and releases the levers 78 to lock the arms 79 of the levers 78 into the pockets 98 and catches 97, as illustrated in FIGS. 8 and 9.

Figure 10A:
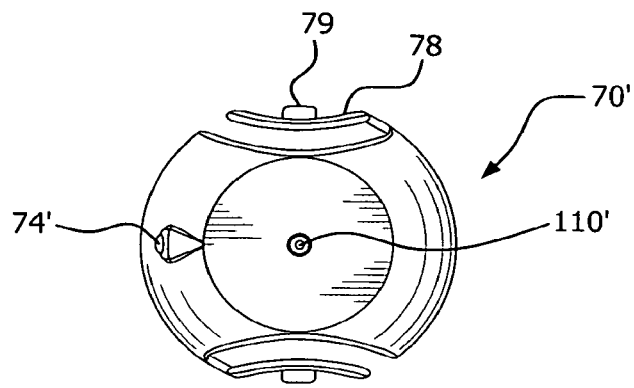
FIG. 10A is a top view of the housing of the infusion set of FIG. 8A.
Figure 10B:
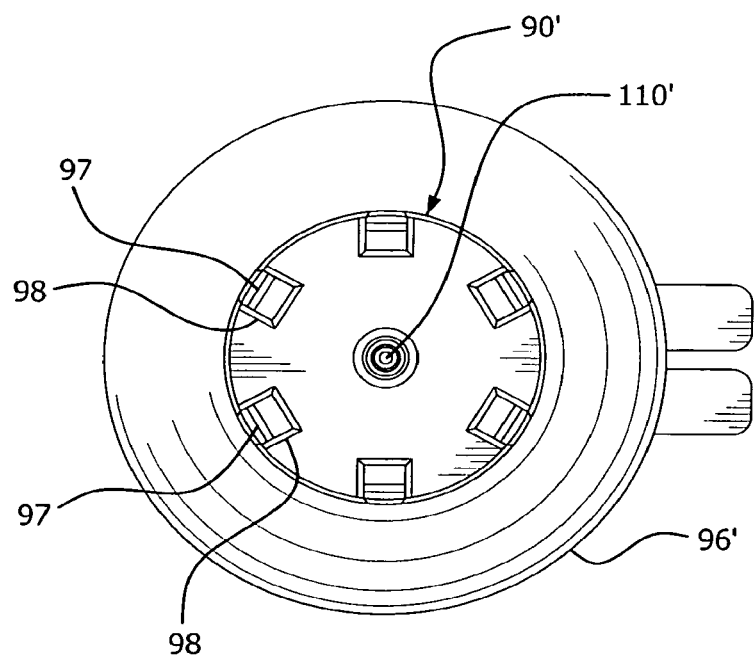
FIG. 10B is a top view of the base of the infusion set of FIG. 8A.

FIG. 10A illustrates a top view of the hub 70' that can attach and detach to and from the base 90' of FIG. 10B. As illustrated in FIG. 10B, there are six distinct rotational positions that the hub 70' can attach to the base 90', corresponding to each of the pockets 98 that the user can select. Such selection will determine at what angle the hub 70' will be oriented when attached to the base 90', and hence the direction in which the connected tubing (not shown) extends. In this embodiment, the increment of rotation that is available is 60 degrees. The number of pockets 98 with corresponding catches 97 will determine the rotational positions of the hub 70' vis-à-vis the base 90'.

As illustrated in FIGS. 8-10, when the hub 70' is attached to the base 90', the pre-slit septum 120' of the base 90' is opened by the blunt cannula 76'. A needle path for the introducer needle 44' is formed when the introducer needle 44' penetrates the cylindrical septum 110', the blunt cannula 76, septum 120' and the catheter 42' during priming.

As illustrated in FIG. 9, the cylindrical septum 110' is preferably cylindrical in shape and parallel with the tube set receiver 74'. The septum 110' provides a seal where the introducer needle 44' is placed, while permitting flow from the tubeset receiver 74 to the blunt cannula 76 and the catheter 42'. The base 90' includes an adhesive pad 96' for attaching the base 90' to the user, as illustrated in FIGS. 8-11.

An advantage of this embodiment is that the release mechanism is integral to the hub 70' and base 90' and facilitates a lower profile due to fewer components. The squeeze action or biasing of the levers 78 is user-friendly and intuitive. In addition, the integrated release mechanism is reliable since there are fewer assembly tolerances to consider, as compared with other latching mechanisms.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention, as defined in the appended claims and their equivalents.

The invention claimed is:
1. An infusion set comprising:
 a housing comprising a housing septum and a blunt cannula;
 a base comprising a base septum, an infusion cannula, and a retention boss into which the blunt cannula passes when the housing is attached to the base;
 a latching device for attaching and detaching the housing to the retention boss, the latching device comprising a movable keyhole slot having a larger diameter portion and a smaller diameter portion, the larger and smaller diameter portions having side walls that completely enclose the movable keyhole slot; and
 a spring, the spring being of unitary construction with the latching device and disposed externally to the movable keyhole slot;

wherein when the housing is attached to the base, the blunt cannula extends into and opens the base septum; and wherein when the housing is attached to the base, an introducer needle can be extended through the housing septum, blunt cannula, base septum and infusion cannula.

2. The infusion set as claimed in claim 1, wherein when the housing is detached from the base, the base septum self-closes.

3. The infusion set as claimed in claim 1, wherein the housing further comprises a tubeset receiver.

4. The infusion set as claimed in claim 3, wherein when the housing is attached to the base, a fluid path is formed that is in communication with the tubeset receiver, base septum, blunt cannula, housing septum and infusion cannula.

5. The infusion set as claimed in claim 1, wherein when the introducer needle is removed after attaching the infusion cannula to a user, the housing septum self-closes.

6. The infusion set as claimed in claim 1, wherein when the housing is attached to the base, the blunt cannula is positioned between the housing septum and the base septum.

7. The infusion set as claimed in claim 1, wherein the retention boss comprises a cap portion and a stem portion.

8. The infusion set as claimed in claim 1, wherein the housing septum is cylindrical in shape.

9. The infusion set as claimed in claim 1, wherein the spring is coplanar with the movable keyhole slot.

10. A latching device for latching a housing and a base of an infusion set, the latching device comprising:
   a release device;
   a retention boss;
   a movable keyhole slot comprising a larger diameter portion and a smaller diameter portion, the larger and smaller diameter portions having side walls that form a closed periphery around the movable keyhole slot, the movable keyhole slot being movable between a first position in which the smaller diameter portion is engaged with the retention boss, and a second position in which the smaller diameter portion is disengaged from the retention boss; and
   a spring, the spring being of unitary construction with the movable keyhole slot, and wherein when the release device is pressed, the release device actuates the spring to move the movable keyhole slot from the first position to the second position;
   wherein the housing comprises the release device and the movable keyhole slot, and the base comprises the retention boss;
   wherein when the release device is pressed, the release device actuates the movable keyhole slot to move from the first position to the second position to unlatch the housing from the base; and
   wherein the spring is disposed externally with respect to the movable keyhole slot.

11. The latching device as claimed in claim 10, wherein the spring comprises a leaf spring.

12. The latching device as claimed in claim 10, wherein the release device comprises a release button.

13. The latching device as claimed in claim 10, wherein when the movable keyhole slot is moved to the second position, the larger diameter portion is adjacent to the retention boss without engaging the retention boss.

14. The latching device as claimed in claim 10, wherein the spring is coplanar with the movable keyhole slot.

15. A latching device for latching a housing and a base of an infusion set, the latching device comprising:
   a release device;
   a retention boss;
   a movable keyhole slot comprising a larger diameter portion and a smaller diameter portion, the movable keyhole slot being movable between a first position in which the smaller diameter portion is engaged with the retention boss, and a second position in which the smaller diameter portion is disengaged from the retention boss, the movable keyhole slot completely surrounding the retention boss in both the first and second positions; and
   a spring externally disposed with respect to the movable keyhole slot and co-planar with the movable keyhole slot;
   wherein the housing comprises the release device and the movable keyhole slot, and the base comprises the retention boss.

16. The latching device as claimed in claim 15, wherein the spring is of unitary construction with the movable keyhole slot.

* * * * *